(12) United States Patent
Caillouette

(10) Patent No.: US 7,101,342 B1
(45) Date of Patent: Sep. 5, 2006

(54) DETECTION OF MENOPAUSE STATUS AND TREATMENT THEREOF

(76) Inventor: James C. Caillouette, 685 Oak Knoll Cir., Pasadena, CA (US) 91106

( * ) Notice: Subject to any disclaimer, the term of this patent is extended or adjusted under 35 U.S.C. 154(b) by 0 days.

(21) Appl. No.: 10/851,017

(22) Filed: May 24, 2004

(51) Int. Cl.
 *A61B 10/00* (2006.01)
(52) U.S. Cl. .................................................. 600/551
(58) Field of Classification Search ........ 600/569–573, 600/562, 584, 551, 591, 547, 587; 604/1; 33/511, 512, 755, 758–760; 514/177; 607/138
 See application file for complete search history.

(56) References Cited

U.S. PATENT DOCUMENTS

| | | |
|---|---|---|
| 2,664,879 A | 1/1954 | Hardy |
| 2,945,491 A | 7/1960 | Gibbs |
| 3,013,656 A | 12/1961 | Murphy, Jr. |
| 3,037,496 A | 6/1962 | Melges |
| 3,117,569 A | 1/1964 | Wegner |
| 3,319,621 A | 5/1967 | Schwerin |
| 3,450,129 A | 6/1969 | Avery et al. |
| 3,507,269 A | 4/1970 | Berry |
| 3,509,872 A | 5/1970 | Truhan |
| 3,777,743 A | 12/1973 | Binard et al. |
| 3,792,699 A | 2/1974 | Tobin et al. |
| 4,010,738 A | 3/1977 | Preti et al. |
| 4,409,182 A | 10/1983 | Macklem |
| 4,457,313 A | 7/1984 | Alter |
| 4,784,158 A | 11/1988 | Okimoto |
| 4,788,985 A | 12/1988 | Manning et al. |
| 4,820,259 A | 4/1989 | Stevens |
| 4,862,899 A | 9/1989 | Bucaro |
| 5,063,930 A | 11/1991 | Nucci |
| 5,147,288 A | 9/1992 | Schiavo |
| 5,425,377 A | 6/1995 | Caillouette |
| 5,577,512 A | 11/1996 | Caillouette |
| 5,660,790 A | 8/1997 | Lawrence et al. |
| 5,664,579 A | 9/1997 | Caillouette |
| 5,735,801 A | 4/1998 | Caillouette |
| 5,738,634 A | 4/1998 | Caillouette |
| 5,762,614 A | 6/1998 | Caillouette |
| 5,782,801 A | 7/1998 | Caillouette |
| 5,827,200 A | 10/1998 | Caillouette |
| 5,916,173 A * | 6/1999 | Kirsner ..................... 600/551 |
| 5,916,176 A | 6/1999 | Caillouette |
| 6,013,036 A | 1/2000 | Caillouette |

(Continued)

FOREIGN PATENT DOCUMENTS

WO   WO-A-97/46878   12/1997

OTHER PUBLICATIONS

Ronald M. Meltzer, "Vulvoganinitis", vol. 1 Chapter 37, 1994.
Ulla Molander, "Urinary Incontinence and Related Urogenital Symptoms in Elderly Women", Scandinavian Association of Obstertricians and Gynecologists, Supplement 158, vol. 72, 1993.

(Continued)

*Primary Examiner*—Max F. Hindenburg
*Assistant Examiner*—Brian Szmal
(74) *Attorney, Agent, or Firm*—William W. Haefliger

(57) ABSTRACT

The method of treating a human female menopausal condition, the steps that include determining need for increasing estrogen level in the blood, from a lower level associated with reduced ovarian estrogen production, the determining including measuring vaginal moisture or urethral fluid pH level, at repeated time intervals over a series of days. A test for FSH level in the blood, during those days, may be made for detection of high level FSH in conjunction with high pH level at the vagina to establish need for estrogen therapy, on a confirmatory basis.

15 Claims, 2 Drawing Sheets

U.S. PATENT DOCUMENTS

| | | |
|---|---|---|
| 6,117,090 A | 9/2000 | Caillouette |
| 6,390,991 B1 | 5/2002 | Caillouette |
| 6,406,441 B1 | 6/2002 | Caillouette |
| 6,544,196 B1 | 4/2003 | Caillouette |
| 2004/0087563 A1* | 5/2004 | Mayerhofer ................ 514/177 |

OTHER PUBLICATIONS

James P. Semmens, MD, Gorm Wagner, MD, "Estrogen Deprivation and Vaginal Function in Postmenopausal Women", 1982.

Gloria Bachmann, "The Estradio Vaginal Ring—A Study of Existing Clinical Data", Maturitas 22 Suppl. (1995) S21-S29, 1995.

Peter Smith, "Estrogens and the Urogenital Tract", Dept. of Obsterics & Gynecology, University Hospital, S-751 85 Uppsala, Sweden, 1993.

Richard Amsel, MD. et al., "Nonspecific Vaginitis—Diagnostic Criterial and Microbial and Epidemiologic Associations", The American Journal of Medicine, vol. 74, Jan. 1983.

Kirk C.S. Chen et al, "Biochemical Diagnosis of Vaginitis: Determination of Diamines in Vaginal Fluid", The Journal of Infectious Diseases, vol. 145, No. 3, Mar. 1982.

Kirk C.S. Chen et al, "Amine Content of Vaginal Fluid From Untreated and Treated Patients With Nonspecific Vaginitis", The American Society for Clinical Investigations, Inc., vol. 63, May 1979, pp. 82 83.

Culley C. Carson, MD, et al, "Current Management of UTI in Women", Contemporary OB/GYN, Fall, 2000, p. 3, p. 17.

James C. Caillouette, MD, et al., "Vaginal pH as a Marker for Bacterial Pathogens and Menopausal Status", American Journal of Obstetrics and Gynecology, 1996, vol. 176, No. 6, pp. 1270-1277.

Montserrat Garcia-Closas, MD, et al., "Epidemiologic Determinants of Vaginal pH", American Journal of Obstetrics and Gynecology, 1998, vol. 180, No. 5, pp. 1060-1066.

* cited by examiner

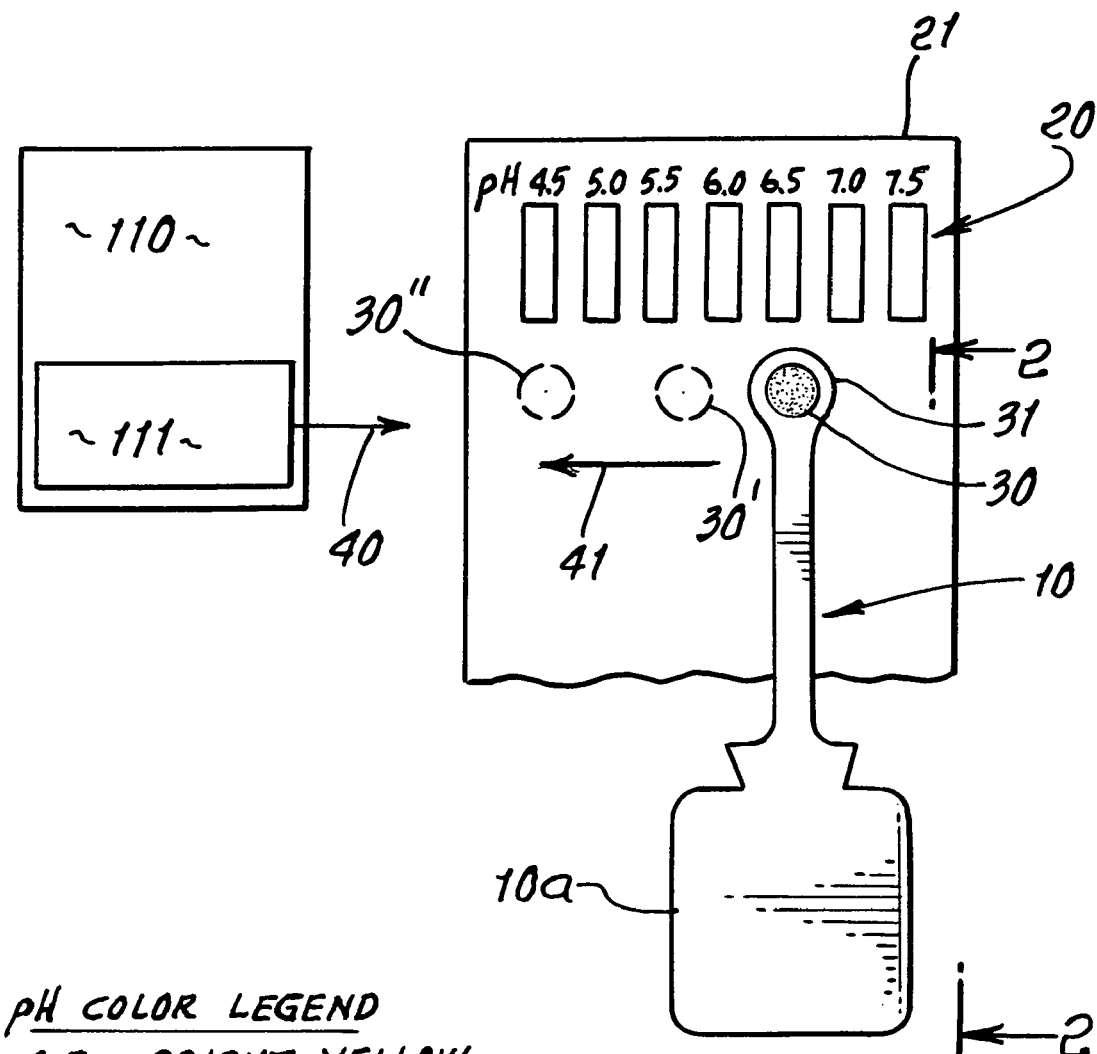

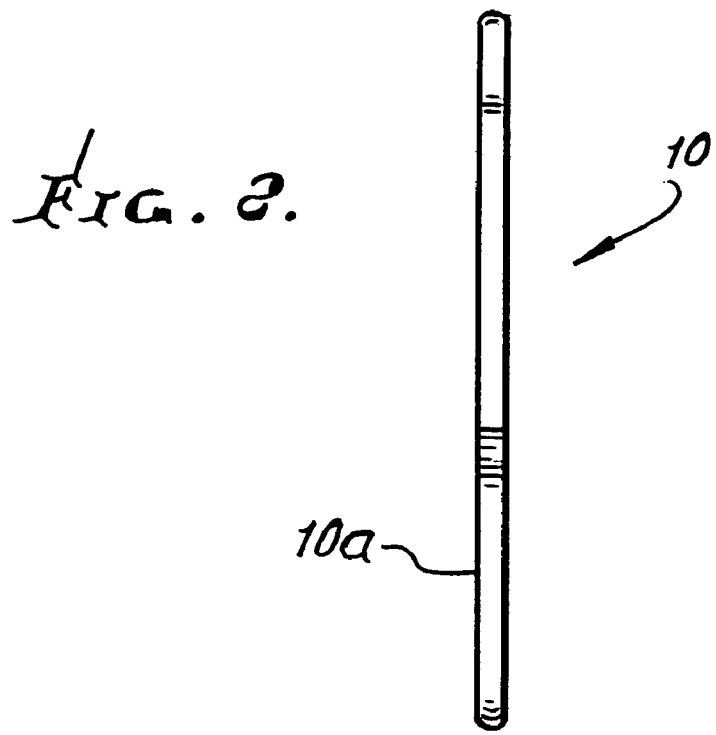
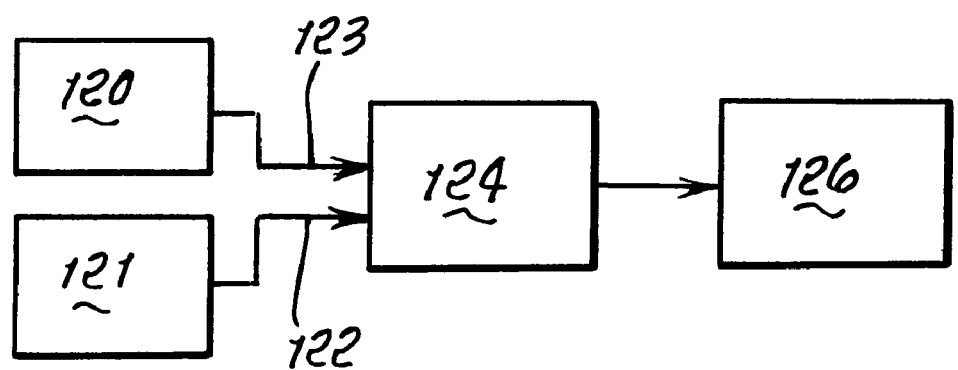

DETECTION OF MENOPAUSE STATUS AND TREATMENT THEREOF

BACKGROUND OF THE INVENTION

This invention relates generally to factors involved in determining estrogen or estradiol administration to human females who are menopausal; and more particularly to a simple and effective diagnostic method and means to effect such determination such as need for changes in dosage of estrogen or estradiol.

There is need for improvements in methods to determine whether or not a human menopausal female should be administered higher or lower levels of estrogen or estradiol. Such need can arise for example in evaluation and diagnosis of female sexual dysfunction (FSD). It appears that lack of estrogen may lead to sexual dysfunction primarily by causing vaginal atrophy and dyspareunia. Another example of need is for treatment of postmenopausal fracture, as in the case of osteoporosis. The present invention addresses such need or needs.

There is also need for a low-cost, diagnostic procedure useful to determine, or screen for, menopausal condition or status, in women, and to provide and monitor a remedy for that condition.

In addition, when FSH level in the blood is monitored, there is need for a simple confirmatory or supplementary test, for estrogen need.

SUMMARY OF THE INVENTION

It is a major object of the invention to provide a self-diagnostic procedure, enabling menopausal women to determine need for estrogen therapy, i.e. need to supply estrogen to the body, to compensate for reduction in ovarian estrogen supply. The needed procedure contemplates a protocol enabling reduction in vaginal pH level from about 6.0 (for menopausal women) to about 4.5, and which may be measured in conjunction with FSH measurement.

It is another object of the invention to provide a method that includes:

a) determining need for increasing estrogen level in the blood, from a lower level associated with reduced ovarian estrogen production, b) said determining including measuring vaginal moisture or urethral fluid pH level, at repeated time intervals over a series of days, for example during estrogen therapy.

For example, the method may include periodically administering estrogen or estradiol to the patient, to be transported in the blood, and such administering is preferably repeated to reduce measured vaginal moisture pH level to about 4.5, or to significantly reduce menopausal symptoms.

An added object of the invention is to measure vaginal moisture acidity by employment of an acidity indicator applied proximate a moist wall surface of the vagina. Such an indicator may advantageously exhibit coloration or colorations corresponding to pH level or levels of moisture at the wall surface of the vagina, such colorations being different for different pH levels.

A further object is to provide a pH measurement calorimeter to be positioned to extend for ready comparison with coloration of the material or materials of the indicator, following its use.

An additional objective is to repeat the vaginal moisture pH measurement at time intervals such that vaginal moisture pH level is ultimately determined to have reached a desired level or levels corresponding to reduced observed menopausal symptoms, in a human patient.

A yet further object is to also measure FSH level in the patient's blood, for correlating an increasing FSH level with an increase in said pH level, as an indicator of need for estrogen increase. Such measuring is typically periodic to indicate a timewise increasing FSH level, for such correlation. Estrogen is then administered to the patient as a result of said correlation, and at a relatively low dosage level corresponding generally to healthy ovarian estrogen production level. Such administering is preferably directly into the blood to maximize the estrogen hormone effect on the body, thereby minimizing the amount of estrogen needed. Measurement correlation as referred to provides a confirmatory (FSH level rising, pH level high or rising) indication of need for estrogen. Correlation of these measurements during estrogen therapy provides confirmation of need for estrogen administration.

A yet further object includes provision of a method of determining need for estrogen administration to a human patient that includes:

a) measuring vaginal moisture pH level, b) measuring FSH level in the blood, c) correlating the a) and b) measurements to determine co-existence of relatively high pH and FSH levels, d) and administering estrogen to the patient as a result of said co-existence correlating.

These and other objects and advantages of the invention, as well as the details of an illustrative embodiment, will be more fully understood from the following specification and drawings, in which:

DRAWING DESCRIPTION

FIG. 1 is a plan view of apparatus incorporated in the method of the invention;

FIG. 2 is a side view taken on lines 2—2 of FIG. 1; and

FIG. 3 is a process flow diagram.

DETAILED DESCRIPTION

FIG. 1 designates generally the step of determining need for increasing estrogen level in the blood, from a lower level associated with reduced ovarian estrogen production level. Numeral 110 designates monitoring or observation of a patient exhibiting one or more menopausal symptoms, needing treatment or reduction, and typically including:

i) insomnia ii) emotional instability iii) body hot flashes iv) vaginal dryness v) urogenital symptoms.

Such FIG. 1 determination includes measuring vaginal moisture, or urethral fluid, pH level, at repeated time intervals, over a series of days. Block 111 schematically designates application of measurement means to the vagina, as by use of the probe 10, which may have the general form of the applicator or probe 10 disclosed in U.S. Pat. No. 6,406,441, incorporated herein by reference.

The test element 30 at the side of the probe, near its tip 31, is employed at 111, as by pressing the element toward and against the vaginal wall. Element 30 typically comprises a pH indicator, and may take the form of a NITRAZINE® strip adhered to the side of the probe, as for example by double sided adhesive tape. After exposure of the strip to vaginal moisture, its changed color (according to pH level) is compared with the series 20 of bands on a support 21.

Each band has a different color corresponding to a pH level color to which the detector strip may change. See for example the indicated pH levels 4.5, 5.0,m 5.5, 6.0, 6.5, 7.0 and 7.5 adjacent the color bands. The bands may be provided on a strip adhered to the outer surface of the support. Paper strips providing such elements are known, and sold under the name HYDRION papers, by Micro Essential Laboratory Inc., Brooklyn, N.Y. 11210. The band for pH 4.5 is typically bright yellow; the band for pH 6.0 is olive in color; and the band for pH 7.5 is navy blue.

Arrow 40 indicates removal of the probe from the vagina, for use as depicted, proximate the calorimeter bands. Arrow 41 indicates periodic progress of a succession of probes and test elements 30 in a direction corresponding to lowered pH level associated with periodic estrogen administration to the menopausal patient. That direction is also an indicator of gradual reduction of menopausal symptoms, whereby when the color of a test element 30 corresponds to the color of the pH 4.5 band, the patient's estrogen deficiency caused menopausal symptoms have been significantly reduced, or eliminated. In this regard, a different probe 10 and/or element 30, is normally employed for each of the periodic tests, so that the element 30 is new, for each test, the different elements indicated for example at 30, 30', and 30", at successive leftward positions. The probe handle is seen at 10a.

In FIG. 3, the block 120 represents the vaginal pH determination including pH self-testing as described above, and as for example is represented in FIG. 1. Block 121 represents a determination of FSH level (follicle stimulating hormone produced by the pituitary) in the blood, as by means of a blood or urine test. In this regard block 121 may represent a simple test for a timewise sequence of such FSH level tests, as over one or more days intervals, to determine a high or rising FSH level to compensate for very low level or non-existent ovarian estrogen output, to the blood.

Block 124, receiving the output 122 and 123 from blocks 120 and 121, represents the step of correlating those outputs, for example observing high measured level (15–17) FSH, and in conjunction with high measured level (6.0–6.2) vaginal pH, these together providing a dual confirmatory basis or reason for need of estrogen administration to the patient. Block 126 represents administration of estrogen to the patient (for example by patch to a limb) as a result of such observed correlation. Such administration can then be initially effected at a relatively low and safer dosage level corresponding generally to healthy ovarian estrogen production level. For example, a low level may be within the range 0.15 to 0.165 milligrams, per day. As estrogen therapy continues, the levels of the measurement outputs at 120 and 121 can be correlated to indicate reduction in both levels to normal, at which the corresponding confirmed estrogen need level is established.

I claim:

1. In the method of treating a human female menopausal condition, the steps that include:
    a) determining need for increasing estrogen level in the blood, from a lower level associated with reduced ovarian estrogen production,
    b) said determining including measuring vaginal moisture or urethral fluid pH level, at repeated time intervals over a series of days,
    c) said determining including providing an elongated probe having an enlarged handle at one end and an enlarged, peripherally generally circular test region at the opposite end of the probe, and a moisture acidity indicator substantially centrally exposed to the exterior, within said test region and at one side of the probe, the indicator characterized as having characteristic coloring that corresponds to moisture acidity,
    d) there being an elongated stem between said test region and said handle, said stem having flat opposite sides and elongated opposite edges of constant thickness diverging toward the substantially circular outer periphery of said test region, said indicator having a substantially circular outer periphery substantially uniformly spaced inwardly of said test region outer periphery whereby the indicator outer periphery is everywhere substantially concentric to the test region substantially circular outer periphery.

2. The method of claim 1 including periodically administering estrogen or estradiol to the patient, to be transported in the blood.

3. The method of claim 2 where said administering is repeated to reduce the measured vaginal moisture pH level to about 4.5, or to significantly reduce menopausal symptoms.

4. The method of claim 1 which further includes periodically observing one or more menopausal symptoms needing reduction, including:
    i) insomnia
    ii) emotional instability
    iii) body hot flashes
    iv) vaginal dryness.

5. The method of claim 1 wherein said measuring of vaginal moisture pH level includes determining local acidity proximate a moist wall surface of the vagina, by employment of said acidity indicator.

6. The method of claim 5, wherein said indicator includes one of the following:
    i) nitrazine paper
    ii) phenaphthazine on a carrier
    iii) a material or materials exhibiting different colorations as a function of pH level.

7. The method of claim 5 including providing a strip of material carrying said acidity indicator, and said determining of local acidity includes first contacting said strip with the wall surface of the vagina, and then observing said indicator.

8. The method of claim 5 wherein said indicator comprises a material or materials exhibiting colorations corresponding to pH levels of moisture of the wall surface of the vagina, said colorations being different for different pH levels.

9. The method of claim 5 including manipulating said probe to bring said indicator into said contact with the vaginal wall surface.

10. The method of claim 8 including providing a pH measurement calorimeter, and positioning said colorimeter to extend for ready comparison with coloration of said material or materials of the indicator.

11. The method of claim 2 wherein said measuring is repeated at time intervals such that vaginal moisture pH level is ultimately determined to have reached a desired level corresponding to reduced observed menopausal symptoms, in a human patient.

12. The method of claim 1 wherein said determining also includes measuring FSH level in the patient's blood, for correlating an increasing FSH level with an increase in said pH level, as an indicator of said need for estrogen increase.

13. The method of claim 12 wherein said FSH measuring is periodic to indicate a timewise increasing FSH level, including said correlating step.

14. The method of claim 13 including administering estrogen to the patient as a result of said correlation, and at a relatively low dosage level corresponding generally to healthy ovarian estrogen production level.

15. The method of determining need for estrogen administration to a human patient that includes:
- a) measuring a timewise increasing vaginal moisture pH level,
- b) measuring a timewise increasing FSH level in the blood,
- c) correlating the a) and b) measurements over time to determine co-existence of relatively high pH and FSH levels,
- d) and administering estrogen to the patient as a result of said co-existence correlating, and initially at a relatively low dosage level,
- e) said step a) measuring including providing an elongated probe having an enlarged handle at one end and an enlarged, peripherally generally circular test region at the opposite end of the probe, and a moisture acidity indicator substantially centrally exposed to the exterior, within said test region and at one side of the probe,
- f) there being an elongated stem between said test region and said handle, said stem diverging toward the generally circular outer periphery of said test region, said indicator having a generally circular periphery substantially uniformly spaced inwardly of said outer periphery,
- g) said indicator periphery and the outer periphery of the test region being substantially concentric.

* * * * *